United States Patent [19]

Stühler et al.

[11] Patent Number: 4,853,430
[45] Date of Patent: Aug. 1, 1989

[54] METHOD OF INCREASING VISCOSITY WITH FATTY ACID-MODIFIED POLYESTERS AND HIGHLY VISCOUS COMPOSITIONS OBTAINED THEREBY

[75] Inventors: Herbert Stühler, Burgkirchen/Alz; Alwin Reng, Kelkheim; Werner Skrypzak, Liederbach; Jochen M. Quack, Eppstein/Taunus, all of Fed. Rep. of Germany

[73] Assignee: Hoechst Aktiengesellschaft, Frankfurt am Main, Fed. Rep. of Germany

[21] Appl. No.: 140,914

[22] Filed: Dec. 30, 1987

Related U.S. Application Data

[62] Division of Ser. No. 527, Jan. 5, 1987, abandoned.

[30] Foreign Application Priority Data

Jan. 8, 1986 [DE] Fed. Rep. of Germany ....... 3600263

[51] Int. Cl.⁴ .................. C08J 67/02; C11D 17/00; A61K 31/74
[52] U.S. Cl. .................. 524/604; 252/173; 252/174.23; 424/78; 514/844; 528/295.3; 528/295.5; 528/274
[58] Field of Search .......... 524/604; 528/295.3, 528/295.5, 274; 252/173, 174, 23; 424/78; 514/844

[56] References Cited

U.S. PATENT DOCUMENTS

| | | | |
|---|---|---|---|
| 2,813,841 | 11/1957 | Parker et al. | 528/295.3 |
| 3,218,296 | 11/1965 | Sidi | 528/245.5 |
| 3,399,153 | 8/1968 | Sekmakas et al. | 528/245.5 |
| 3,784,520 | 1/1974 | Hoeschele | 524/604 |
| 4,274,986 | 6/1981 | Ikenaga et al. | 528/245.5 |
| 4,474,941 | 10/1984 | Wilk et al. | 528/295.3 |

FOREIGN PATENT DOCUMENTS 0143262  11/1981  Japan .................. 524/604

*Primary Examiner*—Morton Foelak
*Assistant Examiner*—Dennis R. Daley

[57] ABSTRACT

Fatty acid-modified polyesters composed of polyalkylene oxide and dimerized fatty acids, of the formula

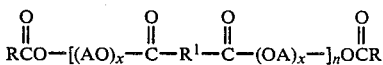

in which R is $C_8$–$C_{22}$-alkyl or $C_8$–$C_{22}$-alkenyl, preferably $C_{12}$–$C_{18}$-alkyl, $R^1$ is the alkyl skeleton of a dimerized fatty acid having 22 to 42, preferably 34 carbon atoms, A is —$C_2H_4$— or —$C_3H_6$—, n is a number from 1 to 5, preferably 1 to 3, and x is a number from 20 to 150, preferably 23 to 140. These are prepared by simultaneous reaction of the underlying dimerized fatty acid, polyalkylene oxide and fatty acid. The polyesters obtained are used as agents for increasing the viscosity of surfactant-containing cosmetic, pharmaceutical and industrial products.

9 Claims, No Drawings

METHOD OF INCREASING VISCOSITY WITH FATTY ACID-MODIFIED POLYESTERS AND HIGHLY VISCOUS COMPOSITIONS OBTAINED THEREBY

This application is a division of application Ser. No. 000,527, filed Jan. 5, 1987, now abandoned.

Water-containing solutions, emulsions or suspensions of surfactants are frequently adjusted to higher viscosity levels in order to improve their application properties. Such mixtures are used, for example, for formulating cosmetic, pharmaceutical and industrial products. The high viscosity of such mixtures facilitates handling, for example in the case of viscous hair shampoo formulations, which then flow off less readily from the hands and the hair. Moreover, they allow a reduction in the quantity used, for example in the case of dishwashing agents, or simplified metering, for example when they are used as laundry softening rinses. In production, filling can additionally be made easier. Further advantages result from the use of viscosity-increasing agents, above all as an improvement in the storage stability of water-containing surfactant systems with water-insoluble active ingredients, for example in anti-dandruff shampoos with zinc pyrithione as the active ingredient.

A large number of so-called thickeners are suggested in the specialist literature for influencing the rheological properties of water-containing surfactant systems.

Electrolytes such as, for example, common salt are known for thickening alkyl ether-sulfates in the production of hair and skin cleansers. Cellulose ethers, fatty acid polyethylene glycol monoesters or diesters, sodium alginate, fatty acid alkanolamides, highly disperse amorphous silica, polymers and similar substances can be used individually or in combination with one another.

These so-called thickeners, however, show a number of disadvantages when used in water-containing surfactant systems. Thus, for example, formulations produced with cellulose ethers are prone to bacterial attack and produce unpleasant "stringy" gels when used. By contrast, inorganic thickeners such as, for example, highly disperse amorphous silica lead to sediments in the finished formulations. The use of electrolytes such as common salt for increasing the viscosity of alkyl ether-sulfate solutions should be mentioned in particular. However, when the finished products are stored in metal containers, these can cause troublesome corrosion phenomena.

It has now been found that polyesters which are prepared from polyethylene glycols and dimeric fatty acids and the terminal OH groups of which are capped with monocarboxylic acids are very particularly suitable for increasing the viscosity of water-containing surfactant systems and do not show the disadvantages described above.

The invention relates to fatty acid-modified polyesters composed of polyalkylene oxide and dimerized fatty acids, of the formula

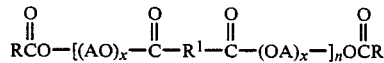

in which R is $C_8$–$C_{22}$-alkyl or $C_8$–$C_{22}$-alkenyl, preferably $C_{12}$–$C_{18}$-alkyl, $R^1$ is the alkyl skeleton of a dimerized fatty acid having 22 to 42, preferably 34 carbon atoms, A is —$C_2H_4$— or —$C_3H_6$—, n is a number from 1 to 5, preferably 1 to 3, and x is a number from 20 to 150, preferably 23 to 140.

These compounds are prepared by combined condensation of a dimerized fatty acid of the formula $$HOOC—R^1—COOH$$

with a polyalkylene oxide of the formula

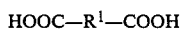

and a fatty acid of the formula

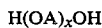

, R, A and x being as defined above.

The dimerized fatty acids used can preferably be the products which are commercially available under the description Pripol (Unichema). These dimerized fatty acids essentially contain linear and cyclic compounds, presumably of the following structure:

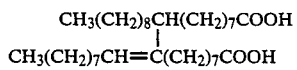

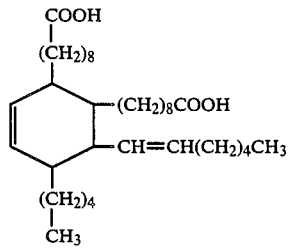

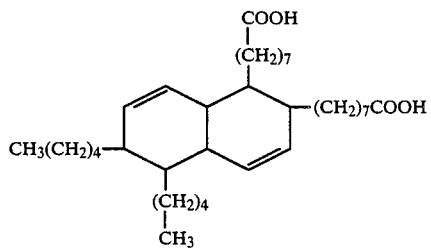

In addition, these products also contain fractions of trimeric and more highly condensed fatty acids. The polyalkylene oxides used are preferably polyethylene oxides, for example polyethylene oxides having a molecular mass of 800, 1,000, 3,000 or 6,000. The fatty acids used are $C_8$–$C_{22}$-fatty acids, preferably saturated $C_{12}$–$C_{18}$-fatty acids and isomeric fatty acids such as isostearic acid.

These compounds are esterified in combination with one another under acid catalysis. The molar ratios of the three starting compounds are 1:2:2 or 2:3:2 or 4:5:2 (dimerized fatty acid:polyalkylene oxide:fatty acid), depending on the desired viscosity level in the use of these polyesters. The esterification is carried out at a temperature of 150° to 200° C., preferably 180° to 190° C., and under a pressure of 80 to 200 mbar, with simultaneous removal of the water of reaction formed. During the reaction, the reaction mixture is blanketed with nitrogen. The acid catalysts used can be the known catalysts and catalyst systems such as, for example, sulfuric acid, Lewis acids or mixtures of dodecylbenzenesulfonic acid/hypophosphorous acid or methanesulfonic acid/hypophosphorous acid. The reaction is monitored by routine determination of the acid number and by measuring the quantity of the water distilled off. The reaction product should have an acid number of at most 3, preferably at most 1. The reaction time required to reach this acid number depends above all on the temperature. In general, it is 18 to 30 hours. After the desired acid number has been reached, the system is advantageously cooled to room temperature as quickly as possible. The polyesters are obtained as slightly yellow-colored products.

These polyesters allow clear, highly viscous formulations of the common non-ionic and/or anionic and/or amphoteric surfactants, for example cosmetic, pharmaceutical and industrial products, to be prepared in a simple manner. The polyesters according to the invention can here be combined with the conventional components of these products. Thus, they can be incorporated, for example, in hair care products, skin cleansers such as, for example, foam bath and shower products, dental cleansers, hair styling products, ointments, dishwashing agents, car cleaning products, domestic cleaning products and other industrial cleaning products. The quantitative content of the polyesters described in the most diverse surfactant-containing products can fluctuate, depending on the desired viscosity, between 0.1 and about 10%, and preferably between 1 and 5%, relative to the weight of the finished formulation. These polyesters are incorporated into the solutions, suspensions or emulsions which are to be thickened, in a manner known per se by dissolving the polyester, if necessary with warming, in the water or water-containing phase.

Finished products which have been adjusted to a higher viscosity by the use of the polyesters according to the invention show the following advantages. An increase in the viscosity of dissolved, suspended or emulsified aqueous solutions of anionic and/or non-ionic and/or amphoteric surfactants is achieved. When used as thickeners, for example in alkyl ether-sulfate solutions, the polyesters show a reduced corrosive effect as compared with common salt, which is frequently used as a thickener. When these polyesters are used for the preparation of highly viscous hair shampoos, a further conditioning effect is obtained after application to the hair, that is to say the hair is easier to comb and styling is facilitated. The aqueous surfactant solutions prepared with the polyesters according to the invention are much less prone to attack by microorganisms such as, for example, bacteria than formulations which have been thickened with cellulose ethers or thickeners of natural provenance, such as agaragar or gelatin. Clear, surfactant-containing, highly viscous finished products can be prepared, whereas inorganic thickeners such as, for example, highly disperse amorphous silica or sodium aluminum silicate cause turbidity and precipitations in the said systems. The polyesters described increase the storage stability of these products, and the dispersibility or handling of these products in use is made easier. In addition, a more pleasant skin sensation after use is obtained. Moreover, the incorporation of the polyesters into water-containing surfactant formulations positively affects the foaming pattern, that is to say a smooth creamy foam is formed which shows a more favorable technological behavior than that obtained with the use of the conventional thickeners.

EXAMPLE 1

150 g of polyethylene glycol 3000, 23.0 g of PRIPOL 1015 dimer acid, 6.1 g is isostearic acid and 0.45 g of methanesulfonic acid and 0.45 g of hypophosphorous acid (50%) as catalysts are introduced into a 1 liter four-necked flask.

The mixture is heated with stirring and nitrogen blanketing to 180° C. and vacuum is applied. The pressure is adjusted to 100 mbar by passing nitrogen through the flask. After a reaction time of 18 hours, a sample is taken for determining the residual acid number. If the acid number is less than 1, the product is cooled to 80° C. and filled into containers.

EXAMPLE 2

300 g of polyethylene glycol 6000, 23.0 g of PRIPOL 1015 dimer acid, 6.1 g of isostearic acid and 0.82 g of methanesulfonic acid and 0.82 g of hypophosphorous acid (50%) as catalysts are introduced into a 1 liter four-necked flask.

The mixture is heated with stirring and nitrogen blanketing to 180° C. and vacuum is applied. The pressure is adjusted to 100 mbar by passing nitrogen through the flask. After a reaction time of 21 hours, a sample is taken for determining the residual acid number. The acid number was less than 1; the product was cooled to 80° C. and filled into containers.

EXAMPLE 3

300 g of polyethylene glycol 6000, 23.0 g of PRIPOL 1015 dimer acid, 15.2 g of isostearic acid and 0.82 g of methanesulfonic acid and 0.82 g of hypophosphorous acid (50%) as catalysts are introduced into a 1 liter four-necked flask.

The mixture is heated with stirring and nitrogen blanketing to 170° C. and vacuum is applied. The pressure is adjusted to 100 mbar by passing nitrogen through the flask. After a reaction time of 25 hours, a sample is taken for determining the residual acid number. The acid number was less than 1; the product was cooled to 80° C. and filled into containers.

EXAMPLE 4

3.7 g of the polyester according to Example 1 are dissolved in 47 g of distilled water, with stirring and warming. 50 g of a 28% solution of a sodium alkyl ethersulfate of the formula $$RO-(CH_2CH_2O)_2-SO_3^{\oplus}Na^{\oplus} z=1-5;$$
$$R=C_8-C_{18}\text{-Alkyl}$$

to which 0.2 g of a perfume oil had previously been added, are then added to the above solution.

The shampoo thus produced shows a viscosity of 2400 mPas, measured at 20° C. in a RVT Brookfield reaction viscometer.

EXAMPLE 5—SHOWER PREPARATION 50 g of a 40% aqueous acylamidoalkyl ether-sulfate triethanolamine salt solution are diluted with 0.3 g of perfume oil and 56.5 g of distilled water. 3.2 g of the polyester mentioned in Example 1 are then dissolved in this mixture with slow stirring and simultaneous warming.

The shower preparation has a viscosity of 1900 mPas at 20° C.

EXAMPLE 6—DISHWASHING AGENT 10 g of secondary sodium alkanesulfonate are dissolved together with 3 g of a sodium alkyl ether-sulfate in 95 g of distilled water, and 2 g of the polyester mentioned in Example 1 are then added to this mixture with stirring and warming.

The dishwashing agent has a viscosity of 850 mPas.

EXAMPLE 7—FOAM BATH 30 g of a 28% alkyldiglycol ether-sulfate solution are mixed with 20 g of a 30% sodium sulfosuccinate-ester, and 44.5 g of water and 0.5 g of perfume oil are then stirred into this solution. Subsequently, 5.0 g of the polyester described in Example 1 are added.

The formulation has a viscosity of 2320 mPas at 20° C.

EXAMPLE 8—FACE CLEANSING LOTION 30 g of a 40% aqueous acylamidoalkyl ether-sulfate triethanolamine salt solution are mixed with 0.3 g of perfume oil and 13 g of a 30% sodium lauroylsarcoside solution. In addition, 0.2 g of allantoin and 51.5 g of water are also stirred into the above mixture. 5.0 g of the polyester described in Example 1 are then added to this solution.

The face cleansing lotion shows a viscosity of 1229 mPas at +20° C.

We claim:

1. A surfactant composition comprising:
   a nonionic, anionic or amphoteric surfactant or a mixture of said surfactants and, as a viscosity-increasing agent therefor,
   a fatty acid-modified polyester which is the reaction product of the components comprising a dimerized fatty acid and a polyalkylene oxide, said fatty acid-modified polyester having the formula

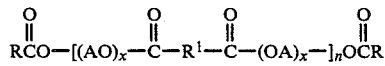

in which R is $C_8$–$C_{22}$-alkyl or $C_8$–$C_{22}$-alkenyl; $R^1$ is the alkyl skeleton of a dimerized fatty acid having 22 to 42 carbon atoms; A is —$C_2H_4$— or —$C_3H_6$—, n is a number from 1 to 5; and x is a number from 20 to 150.

2. A surfactant composition according to claim 1 comprising:
   about 0.1 to about 10% by weight, relative to the weight of the total composition, of a said fatty acid-modified polyester,
   an aqueous phase, in which said fatty acid-modified polyester has been dissolved to increase the viscosity of said phase, and
   said surfactant or mixture of surfactants dissolved, suspended or emulsified in the resulting viscous aqueous phase.

3. A surfactant composition according to claim 1 which is an essentially clear-appearing solution, suspension or emulsion.

4. A surfactant composition according to claim 1, wherein:
   R is $C_{12}$–$C_{18}$ alkyl,
   n is a number from 1 to 3, and
   x is a number from 23 to 140.

5. A surfactant composition according to claim 4, wherein $R^1$ is the alkyl skeleton of a dimerized fatty acid having 34 carbon atoms.

6. A surfactant composition according to claim 1 having a viscosity of at least about 850 mPa·s, measured at 20° C. in an RVT Brookfield reaction viscometer.

7. A surfactant composition according to claim 1, wherein said composition contains an alkyl ether-sulfate or an alkane sulfonate as a said surfactant.

8. A surfactant composition according to claim 7, wherein said alkyl ethersulfate is a sodium alkyl ether-sulfate of the formula RO—(CH$_2$CH$_2$O$_z$)—SO$_3$Na, wherein z is a number from 1 to 5 and R is $C_8$–$C_{18}$ alkyl, or an acylamidoalkyl ether-sulfate or an alkyldiglycol ethersulfate.

9. A cleaning, cosmetic, or pharmaceutical composition comprising:
   a water-containing phase,
   a nonionic, anionic or amphoteric surfactant or a mixture of said surfactants dissolved, suspended or emulsified in said water-containing phase, and, as a viscosity-increasing agent therefor,
   a fatty acid-modified polyester which is the reaction product of the components comprising a dimerized fatty acid and a polyalkylene oxide, said fatty acid-modified polyester having the formula

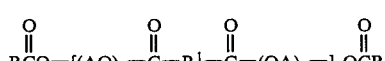

in which R is $C_8$–$C_{22}$-alkyl or $C_8$–$C_{22}$-alkenyl; $R^1$ is the alkyl skeleton of a dimerized fatty acid having 22 to 42 carbon atoms; A is —$C_2H_4$— or —$C_3H_6$—, n is a number from 1 to 5; and x is a number from 20 to 150,
said fatty acid-modified polyester being dissolved in the water-containing phase.

* * * * *